United States Patent
Lukac et al.

(10) Patent No.: US 9,254,174 B2
(45) Date of Patent: Feb. 9, 2016

(54) METHOD FOR LIGHTENING OR ERADICATING PIGMENTS IN HUMAN SKIN

(71) Applicant: Fotona d.d., Ljubljana (SI)

(72) Inventors: Matjaz Lukac, Ljubljana (SI); Zdenko Vizintin, Ljubljana (SI); Boris Cencic, Ljubljana (SI)

(73) Assignee: Fotona d.o.o., Ljubljana (SI)

( * ) Notice: Subject to any disclaimer, the term of this patent is extended or adjusted under 35 U.S.C. 154(b) by 157 days.

(21) Appl. No.: 13/779,857

(22) Filed: Feb. 28, 2013

(65) Prior Publication Data

US 2014/0243804 A1    Aug. 28, 2014

(51) Int. Cl.
*A61B 19/00* (2006.01)
*A61B 18/20* (2006.01)
*A61B 18/00* (2006.01)

(52) U.S. Cl.
CPC ....... *A61B 18/203* (2013.01); *A61B 2018/0047* (2013.01); *A61B 2018/00577* (2013.01)

(58) Field of Classification Search
CPC ........... A61B 2017/00747; A61B 2017/00769; A61B 2017/00154; A61B 2018/00452; A61B 2018/2018; A61B 18/20; A61B 18/203; A61B 2018/0047; A61B 2018/00577; A61B 2018/00601; A61B 2018/2035; A61B 2018/2065; A61B 2018/208; A61B 2018/2085
USPC .............. 606/3, 9; 607/88–94; 128/898
See application file for complete search history.

(56) References Cited

U.S. PATENT DOCUMENTS 8,915,907 B2 *    12/2014    Suckewer .......... A61B 18/203
                                             606/9
2008/0154248 A1 *    6/2008    Dunki-Jacobs ............ 606/9
2009/0069741 A1 *    3/2009    Altshuler .............. A61B 5/441
                                             604/22
2010/0082019 A1 *    4/2010    Neev ........................ 606/9
2013/0172862 A1 *    7/2013    Suckewer ................ 606/9
2014/0005756 A1 *    1/2014    Liu et al. .................. 607/90

OTHER PUBLICATIONS

Marini et al. et al., 'Fractional Er:YAG Skin Conditioning for Enhanced Efficacy of Nd:YAG Q-Switched Laser Tattoo Removal;' Journal of the Laser and Health Academy, vol. 2012, No. 1 (May 2012), pp. 35-40.*
Marini et al.: Fractional Er:YAG Skin Conditioning for Enhanced Efficacy of Nd:YAG Q-Switched Laser Tattoo Removal; Journal of the Laser and Health Acadamy, vol. 2012, No. 1 (May 2012) pp. 35-40.

* cited by examiner

*Primary Examiner* — Ahmed Farah
(74) *Attorney, Agent, or Firm* — Gudrun E. Huckett

(57) ABSTRACT

For lightening or eradicating pigments in human skin, a first conditioning laser optical energy having first optical parameters selected to obtain an ablative effect on the epidermal layer of human skin is provided. A target area of the human skin is conditioned by directing the first conditioning laser optical energy onto the target area and forming in an epidermal layer of the target area discrete pressure and gas release ducts across the target area. A second treatment laser optical energy is provided that has second optical parameters selected to obtain a lightening or eradicating effect on the pigments located within the human skin and to substantially avoid damaging the epidermal layer of the human skin. The second treatment laser optical energy is directed onto the target area subsequent to conditioning, and the pigments within the human skin are lightenmed or eradicated by the second treatment laser optical energy.

28 Claims, 4 Drawing Sheets

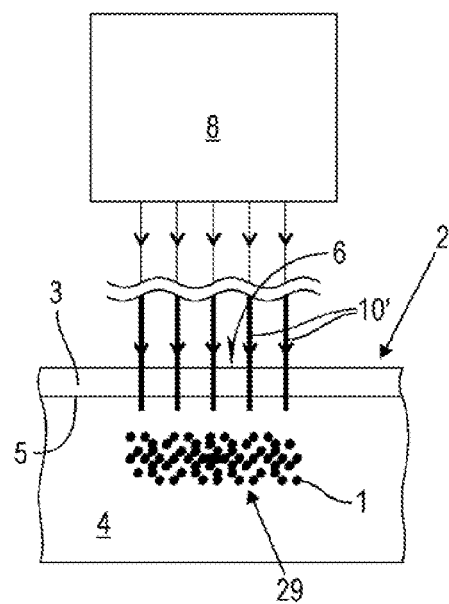 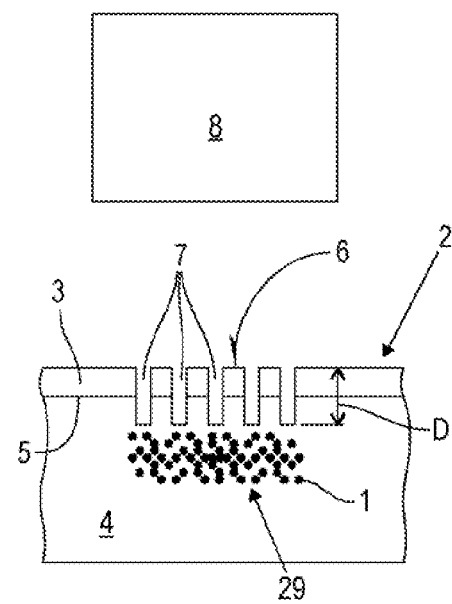 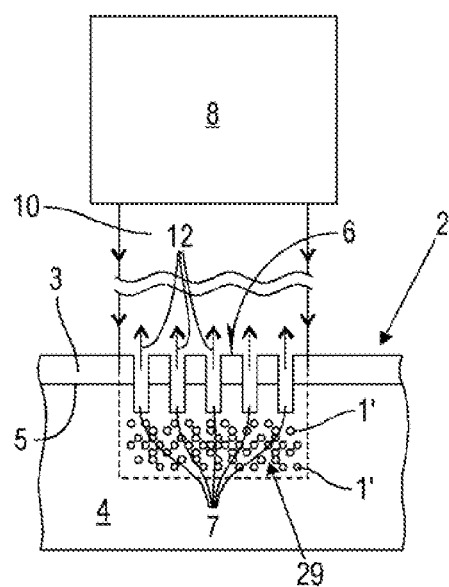 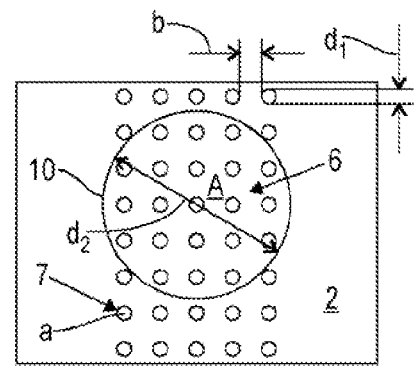 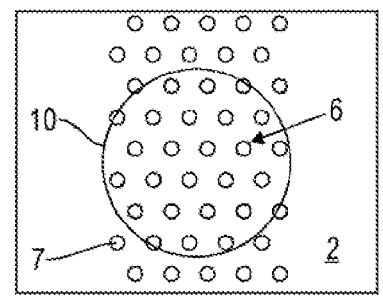
Fig. 5
Fig. 6
Fig. 7
Fig. 8
Fig. 9

METHOD FOR LIGHTENING OR ERADICATING PIGMENTS IN HUMAN SKIN

BACKGROUND OF THE INVENTION

The invention relates to a method for lightening or eradicating pigments in human skin, in particular in pigmented skin lesions or tattoos.

Extremely short pulse (ESP), nanosecond or picosecond laser systems can successfully lighten or eradicate a variety of pigmented lesions. Pigmented lesions that are treatable include freckles and birthmarks including some congenital melanocytic naevi, blue naevi, naevi of Ota/Ito and Becker naevi. The ESP laser systems can also selectively destroy tattoo pigment without causing much damage to the surrounding skin. The altered pigment is then removed from the skin by scavenging white blood cells and tissue macrophages.

One of the techniques by which a laser can be made to produce a pulsed output beam is Q-switching (QS), sometimes known as giant pulse formation. The technique allows the production of light pulses with extremely short (in the range of nanoseconds) pulse duration and high (megawatt) peak power, much higher than can be produced by the same laser operating in continuous wave mode (constant output), or free-running pulse mode (0.1 ms-300 ms). There are also techniques by which laser pulses can be made to the even shorter (in the range of picoseconds). The ESP laser systems are effective because they confine their energy to the treated pigments. The time duration (pulse duration) of the ESP laser energy is so short that the extremely small pigments of a size of 10 nm-100 nm are heated to fragmentation temperature before their heat can dissipate to the surrounding skin. This prevents heating of the surrounding tissue that could potentially lead to burning or scarring of the skin.

The most likely cause of pigment destruction when subjecting the pigments to ESP laser pulses are shockwave and/or cavitation damage, the photomechanical physical effects produced from thermal expansion, and/or the extreme temperature gradients created within the melanosome or tattoo pigment. Melanin absorbs and localizes the high-intensity radiation from ESP lasers, thereby creating a sharp temperature gradient between the melanosome and surrounding structures. This gradient leads to thermal expansion and the generation and propagation of acoustic waves, which mechanically damage the melanosome-laden cells. For the selective removal of pigment, the color of the laser light must penetrate far enough into the skin to reach the target pigment and must be highly absorbed by the pigment relative to the surrounding skin. Different pigments therefore require different laser colors. For example, red light is highly absorbed by green tattoo pigments. In current practice, numerous lasers can specifically target pigmented lesions such lasers including red light lasers (e.g., 694 nm ruby, 755 nm alexandrite), green light lasers (e.g., 532 nm frequency-doubled Nd:YAG), and near-infrared lasers (e.g., 1,064 nm Nd:YAG).

Superficially located pigment is best treated with shorter wavelength lasers whilst removal of deeper pigment requires longer wavelength lasers that penetrate to greater tissue depths. For example, green light lasers (KTP lasers; KTP=potassium titanyl phosphate $KTiOPO_4$) do not penetrate as deeply into the skin as the red light lasers and near-infrared lasers because of their shorter wavelengths. Therefore, green light lasers are effective only in the treatment of epidermal pigmented lesions. Caution should be used when treating darker-skinned people as permanent hypo-pigmentation and depigmentation may occur.

Q-switched Nd:YAG lasers produce a 1,064 nm wavelength beam with a pulse duration of typically 1 nanoseconds-25 nanoseconds. In comparison, pulse durations of QS ruby lasers and alexandrite lasers are typically longer, with durations up to 100 nanoseconds. Although the Nd:YAG wavelength is not absorbed as well by melanin as green light and red light wavelengths, its advantage lies in its ability to penetrate more deeply into the skin (up to 4 mm to 6 mm). A laser which produces 1,064 nm wavelength light is also more useful in the treatment of lesions for individuals with darker skin tones. In addition, the infrared wavelength light produced by a Q-switched Nd:YAG laser system can be converted into visible wavelength light. The latest devices incorporate an Nd:YAG (1,064 nm) laser as the main laser source from which all other wavelengths are created. The first wavelength converter is KTP crystal which has the ability to double the frequency of the incoming Nd:YAG beam and thus produce the halved wavelength of 532 nm (green light). For further wavelength conversions to 585 nm (yellow) and 650 nm (red), the KTP 532 nm laser beam is used as a source for optical pumping of solid-state dye lasers. Recently, solid-state dyes, capable of generating wavelengths other than 585 nm and 650 have also become available.

Picosecond ESP lasers with various wavelengths are also available. An example is an alexandrite laser with a pulse duration of 500 picoseconds to 900 picoseconds which has been used for tattoo removal.

In addition to the appropriate choice of laser color in order to be best absorbed by the color of the pigment, a laser system must be able to deliver extremely short pulses with very high pulse energy. The fluence (F) is one of the main parameters for treating pigments. It is defined as energy density: $F=E/A$, where E is the energy of the laser pulse and A is the spot size area of the laser beam at the skin surface. Sufficient laser fluence must be delivered during each laser pulse to heat the pigment to cause fragmentation. If the fluence is too low, the pigment will not fragment and no removal will take place.

Pigment removal is based on a process of pigment disintegration caused by strong acoustic waves generated during the interaction between ESP laser pulses and the pigment particles. The pigment particles are then more easily removed by the body's own immune system. Several treatment sessions are typically required with intervals of three weeks between sessions to allow the pigment residue to be cleared by the body. It is therefore highly desirable for patients and practitioners to maximize the efficacy of each treatment session and to reduce the number of sessions needed.

One way of possibly increasing treatment efficacy is to increase the energy of the produced acoustic waves by increasing the laser fluence. However, with larger energies of acoustic waves, side effects start to appear more frequently. Cavitation bubbles, which are formed around the pigment particles due to their increased temperature, and plasma formation can damage the surrounding tissue. Measurements of acoustic waves clearly show the existence of a laser fluence threshold at which uncontrolled skin perforation and subsequent scarring as a side effect occur. This threshold represents the limit for the applied laser pulse parameters. Occasional side effects such as depigmentation, allergic reactions, ink darkening, and epidermal debris have been reported as well.

Another option for increasing treatment efficacy is to deliver more than one ESP laser pulse to the treated area during the same treatment session. However, applying a sequence of laser pulses is not as effective as using a single large pulse. Since tissue characteristics change following the irradiation with a laser pulse, the pigment removal efficacy is reduced for subsequent laser pulses. During an ESP pulse, temperatures can exceed 1,000° C. The gaseous products of pyrolysis and superheated steam account for the immediate whitening of the treated skin. Whitening results in an optical shield that prevents subsequent laser pulses from reaching the remaining underlying pigments.

There is therefore the need for an improved method of pigment removal which permits the use of higher laser intensities while reducing the probability of side effects.

SUMMARY OF THE INVENTION

In accordance with the above, the invention provides an improved method for pigment removal, which enables the release of the mechanical wave energy without causing, any damage to the skin. The method is based on (pre)conditioning the skin as a first step in the pigment removal procedure, in a way to prevent damages at higher fluences. Preconditioning (or simply conditioning) is accomplished by making a plurality of discrete micro holes in the skin extending to a depth so as to be close or proximal to the pigments. These micro holes represent pressure release ducts through which internal pressure and gases resulting from the ESP laser treatment can be released without breaking the skin structure. In the second treatment step, a standard ESP treatment laser is applied to remove pigments. Due to (pre)conditioning, higher laser fluences can be used, and multiple subsequent treatments can be performed in the same session.

The conditioning step of the method according to the invention enables the release of the mechanical wave energy without causing any damage to the skin. The introduction of micro ducts or channels for gas and pressure release in the skin during the first step dramatically increases the skin damage threshold. These micro channels act as pressure relief ducts through which the gases, which result from the thermal decomposition of the pigment, can escape without building up excessive pressure. The stress ion the skin or tissue is reduced for the same fluence or the fluence can be increased for the same stress and damage level. The proposed invention has the following advantages:

a) Increased damage threshold of the skin. By preparing channels to allow pressure release, the damage threshold of the skin is enlarged, which means higher fluences can be safely applied. Taking into account that higher fluences are more effective in pigment removal, this means that with a single treatment a higher volume of pigment can be disintegrated and removed.
b) Effective use of multiple treatments in one session. Increased release of dermal intercellular fluid and gases without forming substantial sub-epidermal whitish blisters allows multiple treatments in one treatment session.
c) Increased efficacy of pigment disintegration by inducing multi-center plasma formation. By changing the surface of the skin with a network of ablated channels, the optical properties of the laser beam path are changed as well Multi-center plasma formation can occur which may lead to enhanced mechanical pressure spots in the treated pigment.

Pressure release ducts can be created by using mechanical means, such as a knife or a mechanical drill, or by using an electromagnetic radiation (EMR) source, which source may be a coherent laser light source, an incoherent light source, or a radiofrequency (RF) source. Acoustic sources may also be employed.

Wavelength is a key factor in the suitability of any laser for ablative skin procedures. There are currently three medical laser technologies, namely Er:YAG, Er:YSGG (or Er,Cr: YSGG) and $CO_2$. The laser wavelengths operate in the same ranges as the major absorption peaks for water. Since the skin consists to about 70% of water, these three water-absorbed laser types are most suitable to be used for skin conditioning according to the present invention. But other laser sources may also be used, provided their laser specifications are high enough to achieve skin ablation.

Comparative tests have been performed with two ESP laser treated pig skin spots without and with preconditioning. Violent skin rupture is observed only for the unconditioned spot. For this test, conditioning of the tattooed pig ear was done by making pressure release ducts with a focused Er:YAG laser beam with a beam diameter of 250 micrometers and a fluence of 18 $J/cm^2$. For Er:YAG laser fluences above the ablation threshold fluence of approximately of 1-2 $J/cm^2$, the ablation depth within the skin increases approximately linearly with laser fluence, with a proportionality factor of approximately 4 $\mu m\ cm^2/J$. The approximate depth of the release ducts was therefore around 64 $\mu m$ to 68 $\mu m$, which was sufficient for the relatively superficially located pigments within the pig ear skin. Subsequent pigment removal treatment of both spots was performed with a Q-switched Nd:YAG laser at a laser fluence of 5 $J/cm^2$. It is important to note that without conditioning, skin rupture was observed to occur already at Nd:YAG fluences above 4 $J/cm^2$. In contrast to this, no rupture occurred with Nd:YAG fluences up to 8 $J/cm^2$ when preconditioning was carried out.

Having to use a different conditioning laser source, in addition to the ESP treatment laser, in order to perform skin conditioning prior to pigment removal treatment might not be desirable. However, it was surprisingly found as a preferred embodiment of the invention, that the same laser source can be used both in the treatment step and also for pre-conditioning step of the skin. Based on the teachings of the prior art, the standard ESP treatment lasers, due to their weakly absorbed wavelength and relatively low pulse energies and average powers, would seem unsuitable for thermally induced skin ablation. However, as experimentally confirmed by the inventors, when an ESP laser beam is focused onto a sufficiently small spot, the electric field strength of this focused radiation is high enough to pull electrons out of the atoms, causing plasma to form and producing an optical breakdown with shockwaves disrupting the tissue. The inventors have demonstrated experimentally that preconditioning of the skin is possible with the same Q-switched Nd:YAG (1,064 nm) laser that is subsequently used for pigment removal. In one experiment, 25 pressure release ducts across an area of 10×10 $mm^2$ were made by dividing the incoming Q-switched laser beam by means of a diffraction element into 25 simultaneous individual and discrete beams (pixels) with a diameter of 200 $\mu m$ with a single laser pulse fluence of 91 $J/cm^2$ at each pixel. Four consecutive pulses were delivered to the same area, resulting in a total fluence of 364 $J/cm^2$ delivered at each pixel. According to the invention, pigment removal with preconditioning can therefore be performed using a single laser source to generate both the conditioning laser beam and the treatment laser beam.

Since the body reacts to the "wound" in the form of the ablated skin ducts by releasing blood and other fluids into the skin ducts, it is preferable in view of these bodily responses to deliver the conditioning laser energy in a single short pulse, during which pulse duration the body does not have time to react. However, as demonstrated also by the aforementioned experiment with an ESP laser, it is sometimes advantageous to deliver the conditioning optical energy in the form of a train of consecutive pulses. For example, a train of pulses can be used when the available ESP laser device is not capable of delivering single pulses of sufficiently high energy. When a train of pulses is used, the optical energy of each individual pulse within the train must be near, and preferably above, the threshold energy required to start the ablation process. It is also advantageous when the temporal separation between the pulses is much shorter than the bodily response time, thus avoiding the build-up of bodily fluids within the ablated ducts.

There is another important consideration when using ESP lasers for skin conditioning, which concerns the formation of plasma above the skin at extremely high ESP laser intensities. When plasma is generated at a distance substantially above the skin, it effectively absorbs and blocks the ESP laser light from reaching the skin surface, thus hindering the ablation process. It is therefore advantageous to keep the fluence of the conditioning ESP laser within an optimal range below the threshold fluence required for plasma formation in the air but above the threshold fluence for skin ablation. It is important to note that very close to or at the skin surface, due to the presence of impurities and ejected particles in the air, a limited amount of hot plasma may form already at fluences below the threshold for plasma formation in air. However, since in this case the location of hot plasma is substantially on the skin, this phenomenon may in fact be advantageous in facilitating and accelerating the ablation process. The inventors have shown experimentally that plasma formation in substantially clean air occurs at fluences above approximately 350 $J/cm^2$, while the threshold for skin ablation is at approximately 30 $J/cm^2$. In cases where deep conditioning is desired, this requirement necessitates the use of a train of consecutive ESP pulses instead of a single high-intensity ESP pulse.

BRIEF DESCRIPTION OF THE DRAWINGS

Embodiments of the invention will be explained in the following with the aid of the drawings in more detail.

FIG. 5 shows a schematic cross-sectional view of a pigmented skin portion with a laser source positioned above while delivering, in accordance with the invention, initially conditioning laser optical energy to form in the epidermal layer a plurality of discrete pressure and gas release ducts.

FIG. 6 shows the arrangement according to FIG. 5 with a plurality of discrete pressure and gas release ducts formed by the process step of FIG. 5.

FIG. 7 shows the arrangement according to FIGS. 5 and 6 during the application of multiple subsequent laser pulses for lightening or eradicating the pigments embedded in the skin portion; the generated gas escapes through the pressure and gas release ducts and no shielding effect is observed in contrast to FIG. 4 (prior art).

FIG. 8 shows a schematic top view of the skin portion according to FIGS. 5 to 7 with details of the pressure and gas release duct arrangement and the related treatment beam cross section.

FIG. 9 shows the skin portion of FIG. 8 with an alternative arrangement of the pressure and gas release ducts.

DESCRIPTION OF PREFERRED EMBODIMENTS

Figure 1:
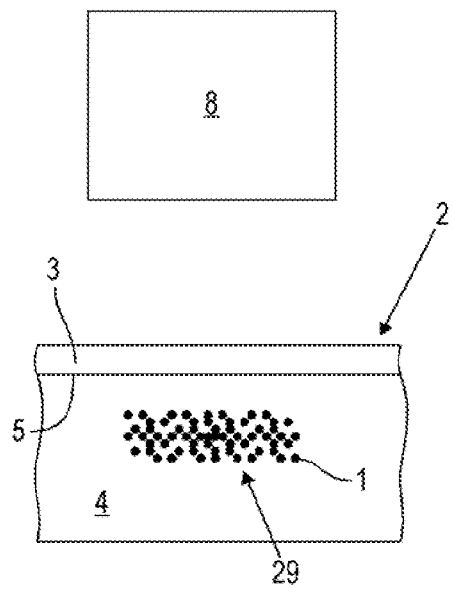
FIG. 1 shows a schematic cross-sectional view of a pigmented skin portion with a laser source positioned above in accordance with the prior art.

FIG. 1 shows in a schematic cross-sectional view a pigmented skin portion with a laser device 8 positioned above in accordance with the prior art. The pigmented skin portion is part of a human skin 2 to be treated, comprising a top epidermal layer 3, a lower dermis 4, and a dermis-epidermis junction 5 in between. Undesired pigments 1 are located below the dermis-epidermis junction 5 within a treatment volume 29 in the dermis 4 at a certain depth relative to the outer skin surface. However, in addition or as an alternative, the treatment volume 29 containing the pigments 1 may be located also in the epidermal layer 3. The treatment volume 29 may contain a pigmented lesion, or a tattoo to be removed, but it could also be some other skin imperfection that can be treated with ESP lasers, such as a melanoma, a vascular lesion, port-wine stain, psoriasis, scar, or other skin blemish. On the epidermal layer 3 a treatment area 6 is defined, which covers the treatment volume 29 beneath that contains the pigment 1 and which is irradiated by laser energy during the course of skin and pigment treatment, as described below.

Figure 2:
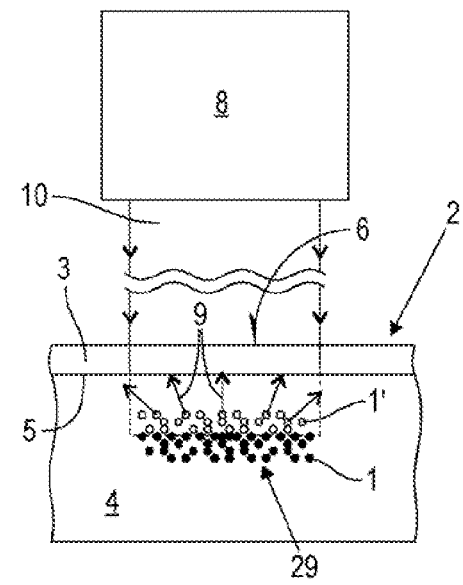
FIG. 2 shows the arrangement according to FIG. 1 during the application of a first laser pulse for lightening or eradicating the pigments embedded in the skin portion (prior art).
Figure 4:
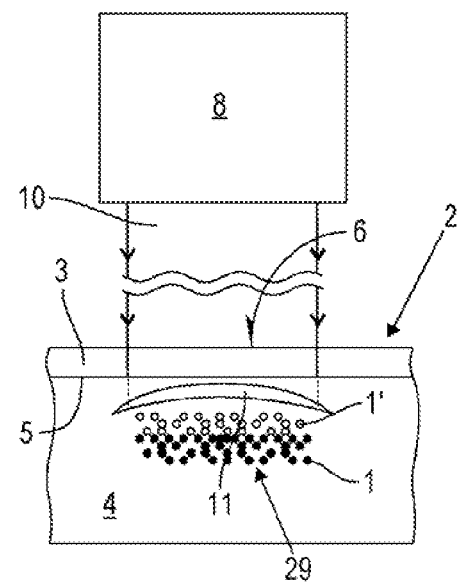
FIG. 4 shows the arrangement according to FIGS. 1 to 3 during the application of a subsequent laser pulse with the whitened tissue portion of FIG. 3 shielding the pigments from the subsequent laser pulse and weakening its effect (prior art).

According to the teachings of the prior art, the pigments 1 are lightened or eradicated by irradiation with a laser beam 10 generated by the laser device 8, as schematically shown in FIGS. 2 and 4. The laser device 8 generates an ESP (extremely short pulse) laser beam 10, with individual pulses having pulse durations in the nanosecond range. FIG. 2 shows the skin 2 at the time when a first pulse of the laser beam 10 is directed onto the treatment area 6, passes through the epidermal layer 3 into the treatment volume 29, and impinges on the pigments 1. The lower embedded pigments 1 are shielded by the top pigments 1' while the top pigments 1' are lightened or eradicated by the first pulse of the laser beam 10. The laser-induced damage of the top pigments 1' leads to the generation of pressurised gas, which penetrates into the surrounding tissue of the skin 2, namely into the dermis 4, as indicated by arrows 9.

Figure 3:
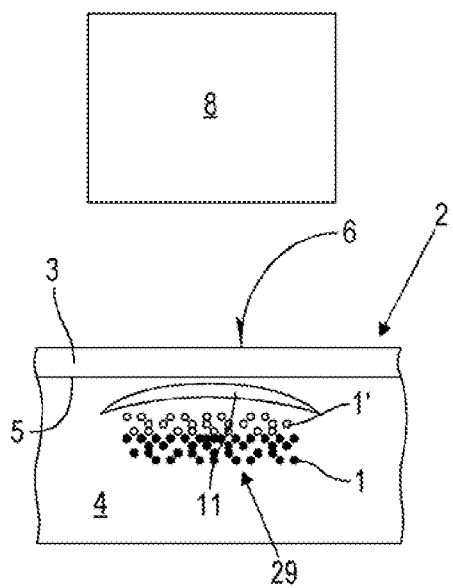
FIG. 3 shows the arrangement according to FIGS. 1 and 2 after the application of a first laser pulse according to FIG. 2 with a whitened tissue portion being formed within the skin as a result of the application of the first laser pulse (prior art).

FIG. 3 shows the arrangement according to FIGS. 1 and 2 after the application of the first laser pulse according to FIG. 2. The aforementioned emerging pressurized gas leads to the formation of a whitened tissue portion 11 within the skin 2, in particular above the pigments 1, 1' facing the epidermal layer 3 and the laser device 8. The whitened tissue portion 11 is at least partially disposed on top of the treatment volume 29, i.e. in the dermis 4 between the pigments 1, 1' and the laser device 8, and may extend into the epidermal layer 3 as well.

FIG. 4 shows the arrangement according to FIGS. 1 to 3 during the application of a subsequent laser pulse; the whitened tissue portion 11 of FIG. 3 has already been generated by the preceding laser pulse according to FIG. 2. As can be seen in FIG. 4, the whitened tissue portion 11 shields the treatment volume 29 including its pigments 1, 1' from the incoming laser beam 10, and this significantly diminishes the lightening or eradicating effect of the laser beam 10 on the residual pigments 1. The lower portion of the treatment volume 29 containing the residual pigments 1 remains more or less untreated.

FIGS. 5 to 9 show in a schematic illustration the inventive method for lightening or eradicating pigments 1 in the human skin 2 as an improvement over the prior art method of FIGS. 1 to 4. In the following, reference numerals remain the same for same or corresponding features in the description and in the drawings. In a first process step, as shown in the schematic view of FIG. 5, a number of individual and discrete laser beams 10' are formed by the laser device 8 and focussed on the target area 6, thereby providing initial conditioning laser optical energy to the epidermal layer 3 and, if desired, to the dermis 4 as well. The conditioning optical energy has optical parameters required for obtaining an ablative effect at least at the epidermal layer 3 and optional at the dermis 4 as well. The optical parameters are described infra in more detail.

The first (initial) conditioning laser optical energy, which is applied to the skin 2 within a target area 6 in form of individual laser beams 10', ablates the skin tissue, thereby forming a plurality of discrete pressure and gas release ducts 7. The number of beams 10' corresponds to the number of ducts 7, as shown in FIG. 6. The pressure and gas release ducts 7 extend from the outer surface of the epidermal layer 3 into the skin 2 with a depth D, at least into the epidermal layer 3. Preferably they extend through the epidermal layer 3 and the dermis-epidermis junction 5 into the dermis 4 to a point close or proximal to the treatment volume 29 with its embedded pigments 1. The release ducts 7 may even extend into the treatment volume 29 containing the pigments 1. The thickness of the epidermal layer varies from 30 μm-300 μm, depending on the location on the body, while tattoo pigments can be located within the skin at a depth of up to 3,000 μm. By selecting the proper optical parameters of the first (initial) conditioning laser optical energy and appropriate focusing of the individual laser beams 10' (FIG. 5), the release ducts 7 are formed. Each duct 7 has a depth D preferably in the range from 30 μm to 3,000 μm and in particular in the range from 50 μm to 300 μm. The focus of the individual laser beams 10' is further adjusted on the target area 6 to a mean diameter $d_1$ corresponding to the same mean diameter of the release ducts 7, as described below in the context of FIG. 8.

The following subsequent process step is schematically shown in FIG. 7. By means of the laser device 8 a second treatment laser optical energy is provided, having optical parameters selected to effect the lightening or eradicating of the pigments 1 located within the human skin 2 and to avoid substantially damage to the epidermal layer 3. The second treatment laser optical energy is directed onto the target area 6 in the form of a full diameter laser beam 10 after the skin 2 has been previously conditioned with the plurality of discrete release ducts 7 within the target area 6 (FIG. 6). The second treatment laser optical energy passes through the epidermal layer 3 into the treatment volume 29 and impinges on the pigments 1 causing them to be destroyed. As mentioned in the context of FIG. 2, the destruction of the pigments 1 leads to the generation of pressurized gas. However, due to the presence of the release ducts 7, the generated gas does not penetrate into the surrounding skin tissue but escapes through the release ducts 7 into the environment, as indicated by arrows 12 in FIG. 7. This avoids the formation of whitened tissue portions 11 according to FIGS. 3 and 4. No optical shielding or gas pressure build-up takes place. Multiple subsequent laser pulses with the second treatment laser optical energy may enter unhindered the treatment volume 29 until all, or almost all, of the pigments 1, 1' have been cleared from the treatment volume 29, as shown in FIG. 7. Thereby, a significant lightening or even a complete eradicating of the pigments 1, 1' is achieved while damage to the epidermal layer 3 and the dermis 4 of the human skin 2 is substantially avoided.

FIG. 8 shows a schematic top view of the skin portion according to FIGS. 5 to 7. In connection with FIG. 5 it can be seen that an irradiation pattern of the individual laser beams 10' has been employed so that the individual release ducts 7 are evenly distributed across the target area 6. According to the embodiment of FIG. 8, a square pattern is chosen. The individual laser beams 10' are focused on the target area 6 with a cross-sectional area, a, and a mean diameter $d_1$. The focus of the individual laser beams 10' (FIG. 5) is adjusted to form the release ducts 7 corresponding to the cross-sectional areas a and the mean diameters $d_1$, the latter being in a range from 50 μm to 1000 μm. It can be further seen that the laser beam 10 providing the second treatment optical energy is shaped to have a beam cross-sectional area A covering multiple discrete pressure and gas release ducts 7 on the target area 6. In particular, the beam cross-sectional area A has, measured on the target area 6, a mean diameter $d_2$ in a range from 3 mm to 15 mm.

An alternative pattern for arranging the release ducts 7 is shown in the schematic top view of FIG. 9. The release ducts 7 are arranged in an equidistant triangular pattern relative to each other. However, any other suitable pattern may be chosen as well. In any case, two adjacent sides of neighboring release ducts 7 are separated by a distance b, preferably in the range from 100 μm to 2,000 μm, and in particular in the range from 200 μm to 900 μm, i.e., immediately neighboring ducts 7 are spaced from each other, or separated from each other, by distance b.

The prior art method according to FIGS. 1 to 4 and the inventive method according to FIGS. 5 to 9 and FIG. 13 were tested in a comparative experiment. It is important to note that without preconditioning (FIGS. 1 to 4, prior art), a skin rupture was observed to occur already at Nd:YAG treatment source fluences above 4 J/cm$^2$; in contrast to this, with the inventive pre-conditioning (FIGS. 5 to 9, 13) no rupture occurred with Nd:YAG treatment source fluences up to 8 J/cm$^2$.

Figure 10:
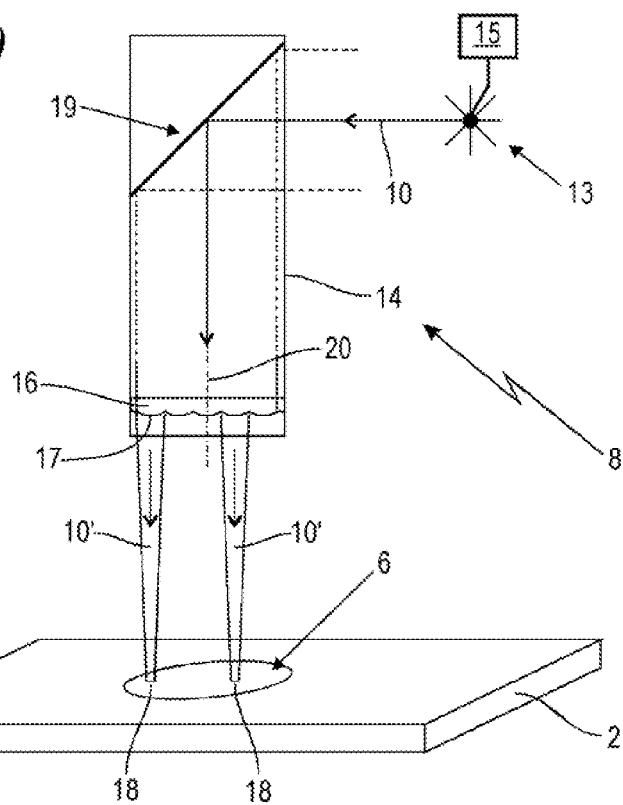
FIG. 10 is a schematic view of a first laser system embodiment for performing the inventive method, comprising a handpiece with a lens array for treating pigmented skin.

FIG. 10 shows in a schematic view a first preferred embodiment of a laser device 8 for performing the inventive method. The laser device 8 comprises an ESP laser source 13 for generating the first conditioning laser optical energy in form of a laser beam 10, a hand piece 14 for manually guiding the laser beam 10 to the target area 6, and an electronic control unit 15 which controls the operation of the laser source 13 for generating the laser beam 10 in an inventive mode as described infra. The ESP laser source 13 is an "extremely short pulse" laser source with pulse durations of less than one microsecond, i.e. in the nanosecond or picosecond range.

For delivering the first conditioning laser optical energy, the hand piece 14 comprises at its distal output end an array 16 of multiple focusing elements 17, here an array 16 of lenses or lens portions in a 5 by 5 matrix as an example. The hand piece 14 further optionally contains a fixed mirror 19 which deflects the incoming laser beam 10 by 90°. However, any other deflection angle may be chosen as well. After being deflected by the mirror 19, the laser beam 10 passes through the hand piece 14 along the longitudinal hand piece axis 20 and further passes through the array 16 of focusing elements 17. The individual focusing elements 17 divide the incoming full-width laser beam 10 into a corresponding number of beam fractions or individual and discrete laser beams 10', each of which is simultaneously focussed by the corresponding lens or focusing element 17 onto a plurality of discrete ablation zones 18 being located on the target area 6. For the sake of simplicity, only two of all discrete laser beams 10' are depicted. Within the discrete ablation zones 18, the skin tissue is substantially simultaneous ablated, thereby forming the release ducts 7 according to FIGS. 5, 6.

In the shown preferred embodiment, both the first conditioning laser optical energy and the second treatment laser optical energy are generated by the same ESP laser source 13. In the present preferred embodiment, the ESP laser source 13 has a wavelength absorbed by the pigments 1 (FIGS. 5 to 7), preferably a wavelength in a range from 0.4 micrometers to 1.1 micrometers. Expediently, the ESP laser source 8 is one of a Q-switched Nd:YAG laser source having a wavelength of 1,064 nm; a frequency-doubled Q-switched Nd:YAG laser source having a wavelength of 532 nm; a dye laser source with a wavelength of 580 nm; a dye laser source with a wavelength of 650 nm; a ruby laser source having a wavelength of 694 nm; and an alexandrite laser source having a wavelength of 755 nm. It will be appreciated by a person skilled in the art, that the array 16 of focusing elements 17 for generating the release ducts 7 will be replaced by a different focusing means, e.g., by a focusing element, such as the focusing element 28 according to FIG. 12, in order to form a full-width laser beam 10 focused on the target area 6 according to FIG. 7 when delivering the second treatment laser optical energy to produce the lightening or eradicating effect on the pigments 1.

Figure 11:
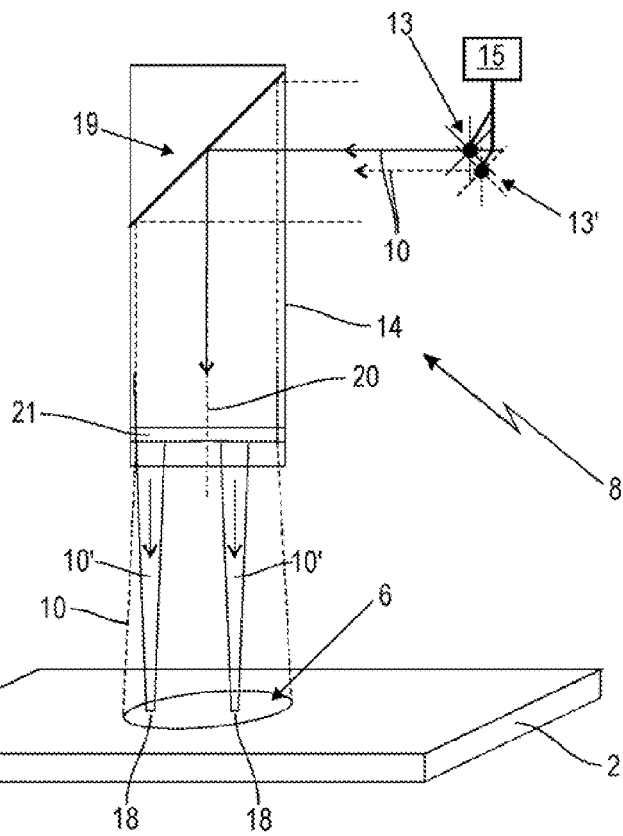
FIG. 11 is a schematic view of a second laser system embodiment for performing the inventive method, comprising a handpiece with a diffraction element for treating pigmented skin.

FIG. 11 shows in a schematic view a second preferred embodiment of a laser device 8 for performing the inventive method. The laser device 8 comprises the laser source 13 as a first laser source and optionally a second laser source 13'. It may be expedient that also the embodiments of FIGS. 10 and 12 comprise, such second laser sources 13'. The array of focusing elements according to FIG. 10 is replaced by a diffraction element 21. The diffraction element 21 allows for the substantially simultaneous generation of multiple discrete and focused laser beams 10' according to FIGS. 5, 8 and 9 while delivering the first conditioning laser optical energy by the first laser source 13, or by the second laser source 13', if present. Similar to what has been described for FIG. 10, the diffraction element 21 for generating the release ducts 7 will be replaced by a different focusing means, e.g. by a focusing element, such as element 28 according to FIG. 12, in order to form a full-width treatment laser beam 10 focused on the target area 6 according to FIG. 7 for the pigment removal step.

The first laser source 13 is the same as described in connection with FIG. 10 and has the same characteristics. It may be used for delivering both the first conditioning laser optical energy and the second treatment laser optical energy. In case of a second laser source 13' being used, the use of the first laser source 13 is limited to generating and delivering the second treatment laser optical energy. The second laser source 13' is then preferably used to generate and deliver the first conditioning laser optical energy, having a water-absorbed wavelength in the range from 2 micrometers to 11 micrometers. Expediently, the second laser source 13' is one of an Er:YAG laser source having a wavelength of 2,940 an Er:YSGG laser source having a wavelength of 2,790 nm; an Er,Cr:YSGG laser source having a wavelength of 2,780 nm; and a $CO_2$ laser source having a wavelength of 9,600 nm to 10,600 nm.

Figure 12:
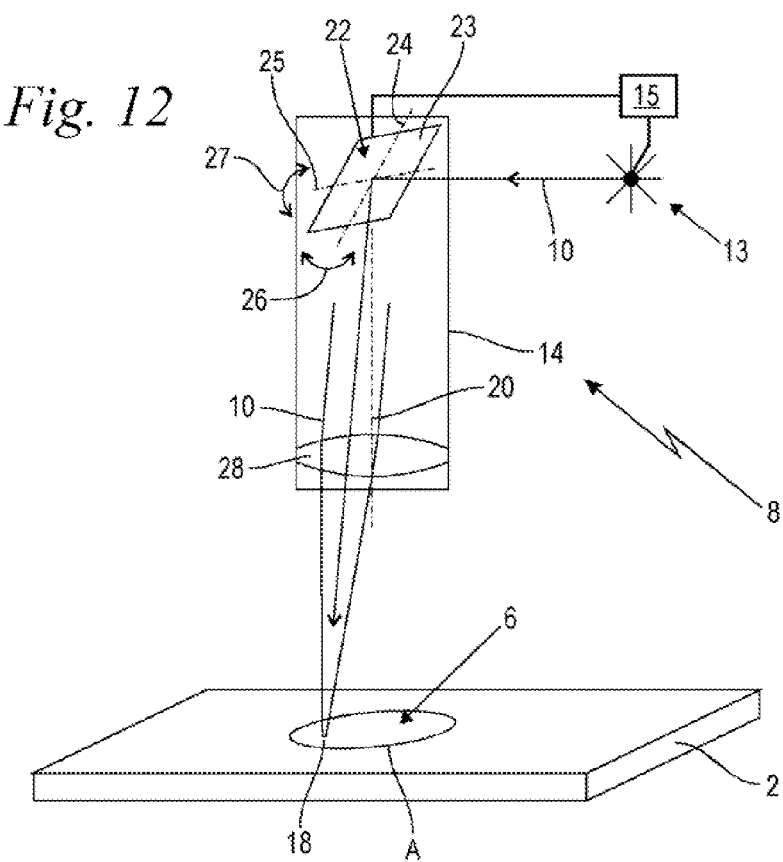
FIG. 12 is a schematic view of a third laser system embodiment for performing the inventive method, comprising a handpiece, a scanner, a lens and a control unit for treating pigmented skin.

FIG. 12 shows in a schematic view a third preferred embodiment of the inventive laser device 8. As shown, a single laser source 13 is provided; in this connection, reference is being had to the explanations in connection with FIG. 10. In lieu of the mirror 19 according to FIGS. 10 and 11, the hand piece 14 contains a scanner 22 with a mirror 23 which is rotationally movable about two axes 24, 25, as indicated by corresponding arrows 26, 27. The axes 24, 25 are perpendicular to each other. In a neutral position without any mirror deflection, the incoming laser beam 10 is deflected by 90°. However, any other neutral deflection angle may be chosen as well. In the neutral position of the scanner mirror 23, the deflected laser beam 10 passes through the hand piece 14 along the longitudinal hand piece axis 20 and further passes a single focusing element 28 in form of a lens or lens arrangement that is disposed at the distal output end of the hand piece 14. The generated laser beam 10 is focused on the target area 6. Upon controlled movement of the scanner mirror 23, the laser beam 10 is deflected to any desired angle relative to the longitudinal hand piece axis 20. The movements of the scanner 22 and the mirror 23 are controlled by the (electronic) control unit 15 in such a manner, that, with the hand piece 14 resting in a certain position without any movement relative to the target area 6, the target area 6 is irradiated in any desired shape and intensity distribution by the focused laser beam 10 based on the control action performed by the correspondingly adapted control unit 15. Thereby, in the conditioning process step when delivering the first conditioning laser optical energy to the human skin target area 6, the target area 6 is scanned in a scanning pattern corresponding to the pattern of the release ducts 7 according to FIGS. 8, 9 to form the release ducts 7. Furthermore, in the subsequent treatment process step, when delivering the second treatment laser optical energy to the human skin target area 6 being already conditioned with the plurality of discrete pressure and gas release ducts 7, the target area 6 is scanned in a scanning pattern to irradiate the skin 2 corresponding to the beam cross-sectional area A as shown in FIG. 8, 9 for lightening or eradicating the pigments 1 located within the human skin 2.

The single focusing element 28 can be, as an option, a zoom lens arrangement. This may allow for focusing the incoming laser beam 10 on the target area 6 with a beam cross-sectional area A and/or a mean beam diameter $d_2$, as shown in FIG. 8 during the treatment process step. In such an embodiment, the use of the scanner 22 may be omitted when delivering the second treatment laser optical energy, i.e. the installed scanner may act as a fixed mirror without scanning movement. As an alternative to the zoom lens arrangement, a fixed focus lens arrangement may be installed for the treatment process step, having the appropriate optical characteristics for imaging the incoming laser beam 10 onto the target area 6 with the full-width beam cross-sectional area A and/or the mean beam diameter $d_2$, as shown in FIG. 8. This again makes the use of a scanner 22 obsolete for the treatment process step.

Figure 13:
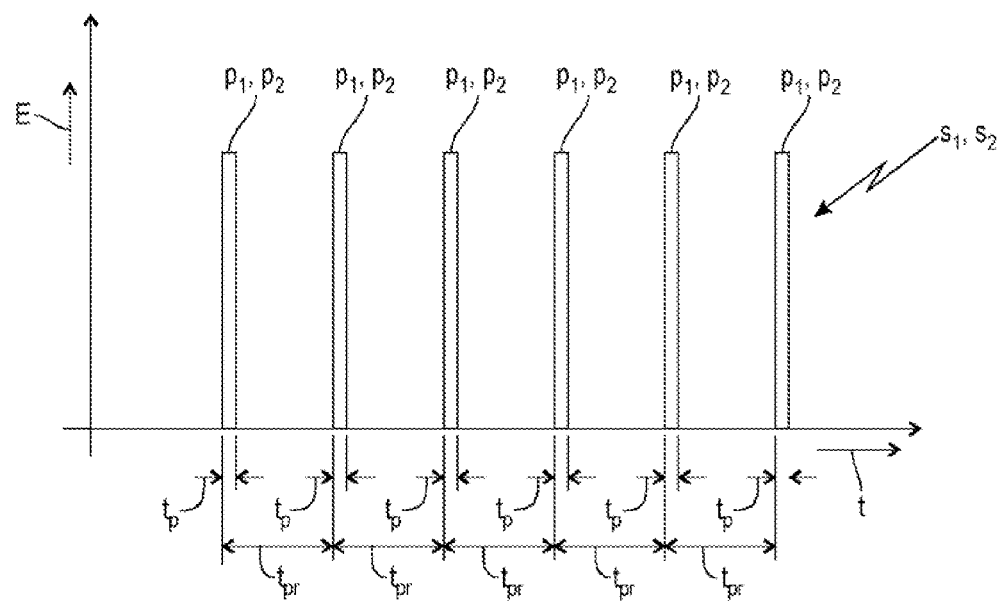
FIG. 13 is a diagram showing an inventive pulse sequence with individual laser pulses to perform the inventive method.

The laser source 13 and/or the laser source 13' are/is controlled by the control unit 15 in such a manner that the laser beams 10, 10' are generated in single pulses p, as shown in the diagram of FIG. 13. In the diagram of FIG. 13, the emitted laser energy E and its distribution over time t is shown, wherein the energy E is typically measured in Joule. Single pulses p or pulses p in a consecutive sequence of any desired sequence length may be generated. In the preferred embodiment according to FIG. 13, a number of pulses p are summarized in temporal conditioning pulse trains or sequences $s_1$, when delivering the first conditioning laser optical energy, or in temporal treatment pulse trains or sequences $s_2$, when delivering the second treatment laser optical energy.

When using the aforementioned first ESP laser source 13 according to FIGS. 10, 12 for the first conditioning process step, the first conditioning laser optical energy is delivered to the target area 6 in the form of a single conditioning pulse $p_1$, or in the form of a temporal conditioning pulse train $s_1$, preferably with 2 to 10 consecutive pulses $p_1$. Such individual conditioning pulses $p_1$ preferably have focused and measured on the target area 6, a fluence in the range from 30 J/cm² to 350 J/cm², this range being above the skin ablation threshold but below the threshold for plasma formation in the air. In the present conditioning process step, when forming the release ducts 7 (FIGS. 5, 6), the fluence is determined by energy E of the single pulse $p_1$ (FIG. 13) of each discrete laser beam 10' (FIG. 5), divided by the cross-sectional area a of one individual discrete release duct 7 (FIG. 9), the latter corresponding to the cross-sectional area of one individual discrete or fraction laser beam 10' (FIG. 5) and also corresponding to the cross-sectional area of one individual discrete ablation zone 18 (FIGS. 10 to 12). The individual conditioning pulses $p_1$ expediently have a pulse duration $t_p$ in the range from 0.5 nanoseconds to 100 nanoseconds, more preferably in the range from 0.5 nanoseconds to 25 nanoseconds.

When using the aforementioned second water-absorbed laser source 13' according to FIG. 11 for the first conditioning process step, the first conditioning laser optical energy is delivered to the target area 6 preferably in the form of a single pulse $p_1$, with the laser fluence adjusted to obtain the desired ablation depth D (FIG. 6). In case the particular laser source 13' is not capable of achieving the required fluence in a single conditioning pulse $p_1$, the conditioning laser optical energy may be delivered to the target area in the form of a temporal conditioning pulse train $s_1$ preferably with 2 to 100 consecutive conditioning pulses $p_1$. The fluence is preferably in the range of 7.5 J/cm² to 750 J/cm², corresponding to the preferred range of depths D of 30 μm to 3,000 μm. In this conditioning set-up, the fluence is defined as the energy E of the single conditioning pulse $p_1$ (FIG. 13) of one discrete laser beam 10' (FIG. 5), multiplied by the number of conditioning pulses $p_1$ in case of a pulse train $s_1$, and divided by the cross-sectional area of one individual discrete ablation zone 18 (FIGS. 10 to 12). The individual conditioning pulses $p_1$ of the conditioning pulse train $s_1$ expediently have a pulse duration $t_p$ in the range from 10 microseconds to 2,000 microseconds.

The individual conditioning single conditioning pulses $p_1$ preferably follow each other at a pulse repetition time $t_{pr}$ that is shorter than approximately 300 ms in order to prevent a build-up of bodily fluid within the ablated ducts in between the pulses.

In both cases of either using the first ESP laser source 13 or the second laser source 13' for delivering the first conditioning laser optical energy, the aforementioned first ESP laser source 13 according to FIGS. 10 to 12 is used for the subsequent treating process step. The second treatment laser optical energy is delivered to the target area 6 in the form of a single pulse $p_2$ or in the form of a temporal treatment pulse train $s_2$, preferably with 2 to 5 consecutive pulses $p_2$. Such individual pulses $p_2$ of the treatment pulse train $s_2$ preferably have, focused and measured on the target area 6, a fluence in the range from 3 J/cm² to 10 J/cm². In the present treatment process step, when lightening or eradicating the pigments 1 (FIG. 7), the fluence is determined through the single pulse energy E (FIG. 13) of the treatment beam 10, divided by the cross-sectional area A of the full-width treatment laser beam 10, as focused on the target area 6 according to FIG. 8. The individual pulses $p_2$ of the treatment pulse train $s_2$ expediently have a pulse duration $t_p$ in the range from 0.5 nanoseconds to 100 nanoseconds, more preferably in the range from 0.5 nanoseconds to 25 nanoseconds.

While specific embodiments of the invention have been shown and described in detail to illustrate the inventive principles, it will be understood that the invention may be embodied otherwise without departing from such principles.

What is claimed is:

1. A method for lightening or eradicating pigments in human skin, the method comprising:
    providing a first conditioning laser optical energy having first optical parameters selected to obtain an ablative effect on the epidermal layer of human skin;
    conditioning a target area of the human skin by directing the first conditioning laser optical energy onto the target area and forming in an epidermal layer of the target area a plurality of discrete pressure and gas release ducts distributed across the target area;
    providing a second treatment laser optical energy having second optical parameters selected to obtain a lightening or eradicating effect on the pigments located within the human skin and to avoid damaging the epidermal layer of the human skin;
    subsequent to the step of conditioning, directing the second treatment laser optical energy onto the target area and lightening or eradicating the pigments within the human skin by the second treatment laser optical energy.

2. The method of claim 1, wherein the discrete pressure and gas release ducts are formed with a depth in a range of 30 micrometers to 3,000 micrometers.

3. The method of claim 1, wherein the discrete pressure and gas release ducts are formed with a depth in a range of 50 micrometers to 300 micrometers.

4. The method of claim 1, wherein the discrete pressure and gas release ducts that are immediately neighboring each other are separated from each other by a distance in a range of 100 micrometers to 2,000 micrometers.

5. The method of claim 1, wherein the discrete pressure and gas release ducts that are immediately neighboring each other are separated from each other by a distance in a range of 200 micrometers to 900 micrometers.

6. The method of claim 1, wherein the discrete pressure and gas release ducts have a diameter in a range from 50 micrometers to 1,000 micrometers.

7. The method of claim 1, wherein the step of conditioning includes focusing with an array of focusing elements the first conditioning laser optical energy simultaneously onto a plurality of discrete ablation zones to form the discrete pressure and gas release ducts.

8. The method of claim 1, wherein the step of conditioning includes focusing with a diffraction element the first conditioning laser optical energy simultaneously onto a plurality of discrete ablation zones to form the discrete pressure and gas release ducts.

9. The method of claim 1, wherein the step of conditioning includes scanning with a scanner coupled to a focusing element the first conditioning optical laser energy across the target area to form the discrete pressure and gas release ducts.

10. The method of claim 1, wherein the step of conditioning includes delivering the first conditioning optical energy to the target area as a temporal pulse train comprising individual single pulses that follow each other in a pulse repetition time shorter than 300.0 ms.

11. The method of claim 1, wherein the step of directing includes applying the second treatment laser optical energy with a beam cross-sectional area covering multiple discrete pressure and gas release ducts on the target area.

12. The method of claim 11, wherein the beam cross-sectional area a mean diameter in a range from 3 mm to 15 mm has on the target area.

13. The method of claim 1, further comprising the step of generating the second treatment laser optical energy with an ESP laser source having a pigment-absorbed wavelength in a range from 0.4 micrometers to 1.1 micrometers.

14. The method of claim 13, wherein the ESP laser source is selected from the group consisting of a Q-switched Nd:YAG laser source having a wavelength of 1,064 nm; a frequency-doubled Q-switched Nd:YAG laser source having a wavelength of 532 nm; a dye laser source with a wavelength of 580 nm; a dye laser source with a wavelength of 650 nm; a ruby laser source having a wavelength of 694 nm; and an alexandrite laser source having a wavelength of 755 nm.

15. The method of claim 13, wherein the step of directing includes delivering the second treatment laser optical energy to the target area in a single treatment pulse or in 2 to 5 consecutive treatment pulses ($p_2$).

16. The method of claim 15, wherein the treatment pulses each have on the target area a fluence in a range from 3 $J/cm^2$ to 10 $J/cm^2$.

17. The method of claim 15, wherein the treatment pulses each have a pulse duration in a range from 0.5 nanoseconds to 100 nanoseconds.

18. The method of claim 15, wherein the treatment pulses each have a pulse duration in a range from 0.5 nanoseconds to 25 nanoseconds.

19. The method of claim 13, wherein both the first conditioning laser optical energy and the second treatment laser optical energy are generated by the same ESP laser source.

20. The method of claim 19, wherein the first conditioning laser optical energy is delivered to the target area in a single conditioning pulse or in 2 to 10 consecutive conditioning pulses.

21. The method of claim 20, wherein the conditioning pulses each have on the target area a fluence in a range from 30 $J/cm^2$ to 350 $J/cm^2$.

22. The method of claim 20, wherein the conditioning pulses each have a pulse duration in a range from 0.5 nanoseconds to 100 nanoseconds.

23. The method of claim 20, wherein the conditioning pulses each have a pulse duration in a range from 0.5 nanoseconds to 25 nanoseconds.

24. The method of claim 1, wherein the step of conditioning includes generating the first conditioning laser optical energy with a conditioning laser source having a water-absorbed wavelength in a range from 2 micrometers to 11 micrometers.

25. The method of claim 24, wherein the conditioning laser source is selected from the group consisting of an Er:YAG laser source having a wavelength of 2,940 nm; an Er:YSGG laser source having a wavelength of 2,790 nm; an Er,Cr:YSGG laser source having a wavelength of 2,780 nm; and an $CO_2$ laser source having a wavelength of 9,600 to 10,600 nm.

26. The method of claim 24, wherein the step of conditioning includes delivering the first conditioning laser optical energy to the target area in a single conditioning pulse or in 2 to 100 consecutive conditioning pulses.

27. The method of claim 26, wherein a cumulative delivered fluence on the target area of all of the conditioning pulses is in a range of 7.5 $J/cm^2$ to 750 $J/cm^2$.

28. The method of claim 26, wherein the conditioning pulses have a pulse duration in a range from 10 microseconds to 2,000 microseconds.

* * * * *